United States Patent
Ohishi

(10) Patent No.: US 7,269,246 B2
(45) Date of Patent: Sep. 11, 2007

(54) X-RAY ANGIOGRAPHY APPARATUS

(75) Inventor: Satoru Ohishi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/558,157

(22) Filed: Nov. 9, 2006

(65) Prior Publication Data

US 2007/0104317 A1  May 10, 2007

(30) Foreign Application Priority Data

Nov. 10, 2005 (JP) ............................ 2005-326336

(51) Int. Cl.
*H05G 1/64* (2006.01)

(52) U.S. Cl. ............... 378/98.12; 378/196; 600/431

(58) Field of Classification Search ............... 378/4, 378/8, 15, 62, 95, 98.12, 193, 195, 196, 207, 378/901; 600/407, 425, 431; 382/130

See application file for complete search history.

(56) References Cited

U.S. PATENT DOCUMENTS

2005/0046644 A1  3/2005  Ohishi ..................... 345/643
2006/0120507 A1  6/2006  Brunner et al. ............ 378/62

FOREIGN PATENT DOCUMENTS

| JP | 2003-334187 | 11/2003 |
| JP | 2004-171283 | 6/2004 |
| WO | WO 03/041583 A2 | 5/2003 |
| WO | WO 2005/110231 A1 | 11/2005 |

*Primary Examiner*—Courtney Thomas
(74) *Attorney, Agent, or Firm*—Oblon, Spivak, McClelland, Maier & Neustadt, P.C.

(57) ABSTRACT

An X-ray angiography apparatus includes a C-arm, a support mechanism which rotatably supports the C-arm, a rotation driving unit which drives rotation of the C-arm, an X-ray tube mounted on the C-arm, an X-ray detector mounted on the C-arm in a direction to face the X-ray tube, and a rotation control unit which controls the X-ray detector and the rotation driving unit to make the angle sampling pitch of contrast images become larger than that of mask images.

20 Claims, 8 Drawing Sheets

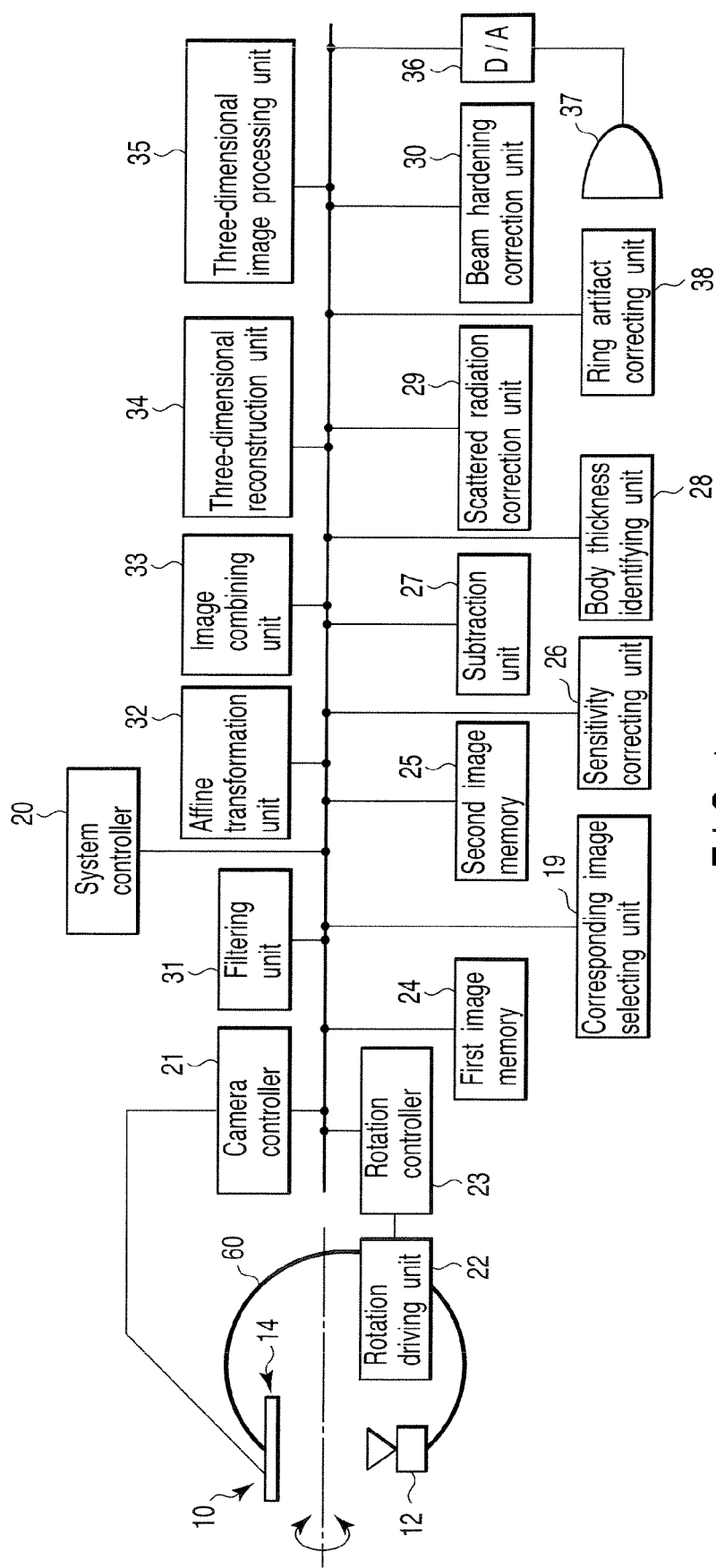
F I G. 1

X-RAY ANGIOGRAPHY APPARATUS

CROSS-REFERENCE TO RELATED APPLICATIONS

This application is based upon and claims the benefit of priority from prior Japanese Patent Application No. 2005-326336, filed Nov. 10, 2005, the entire contents of which are incorporated herein by reference.

BACKGROUND OF THE INVENTION

1. Field of the Invention

The present invention relates to an X-ray angiography apparatus for generating a three-dimensional blood vessel image from images obtained before and after contrast medium injection.

2. Description of the Related Art

The blood vessels in the head run in a very complicated manner. In a case of an aneurysm, in particular, an operator often performs 3D-DSA (three-dimensional digital subtraction angiography) to determine an optimal observation angle which allows to check the neck of the aneurysm or comprehend the relationship between the neck and the dome or between the aneurysm and the parent vessel/capillary vessels near the aneurysm.

In 3D-DSA, the operator acquires a plurality of images in subtraction imaging directions before and after contrast medium injection by repeatedly performing acquisition while rotating an X-ray tube around the patient. In general, a two-dimensional projection image which is acquired before contrast medium injection such that the blood vessels are not contrasted is called a mask image, and a two-dimensional projection image which is acquired after contrast medium injection such that the blood vessels are contrasted is called a contrast image. Subtracting images before and after contrast medium injection upon aligning them in the same imaging directions makes it possible to mainly subtract a contrasted blood vessel portion. This method then generates a detailed three-dimensional blood vessel image by performing three-dimensional reconstruction processing for the extracted image of the blood vessel portion. This three-dimensional image is called a 3D-DSA image. 3D-DSA acquisition or rotational DSA, which is a basic technique thereof, is a technique of observing and reconstructing images upon subtracting images at the same angles. For this reason, mask images and contrast images are always acquired at the same angle sampling pitch.

There has been proposed a method of improving the visibility of a soft tissue by acquiring many projection images, e.g., 400 to 500 frames, and reconstructing a three-dimensional image from the many projection images using an X-ray angiography apparatus. In order to acquire projection images of 400 frames or more, it is necessary to rotate the arm slowly under the limitation of the acquisition rate on the X-ray detector side.

Rotating the arm slowly, however, will inevitably increase the amount of contrast medium used. At the time of diagnosis of disease in a blood vessel system, the operator performs imaging with a small number of projection images in clinical operation, inevitably resulting in a deterioration in the visibility of the soft tissue; refer to Jpn. Pat. Appln. KOKAI Publication No. 2004-171283.

BRIEF SUMMARY OF THE INVENTION

It is an object of the present invention to generate a high-resolution three-dimensional image of a tissue together with a three-dimensional blood vessel image in an X-ray angiography apparatus which generates a three-dimensional blood vessel image from images before and after contrast medium injection.

According to the present invention, there is provided an X-ray angiography apparatus comprising a C-arm, a support mechanism which rotatably supports the C-arm, a rotation driving unit which drives rotation of the C-arm, an X-ray tube mounted on the C-arm, an X-ray detector mounted on the C-arm in a direction to face the X-ray tube, and a rotation control unit which controls the X-ray detector and the rotation driving unit to make an angle sampling pitch of contrast images become larger than that of mask images.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of an X-ray angiography apparatus according to an embodiment;

DETAILED DESCRIPTION OF THE INVENTION

An X-ray angiography apparatus according to a preferred embodiment of the present invention will be described below with reference to the views of the accompanying drawing.

Figure 2:
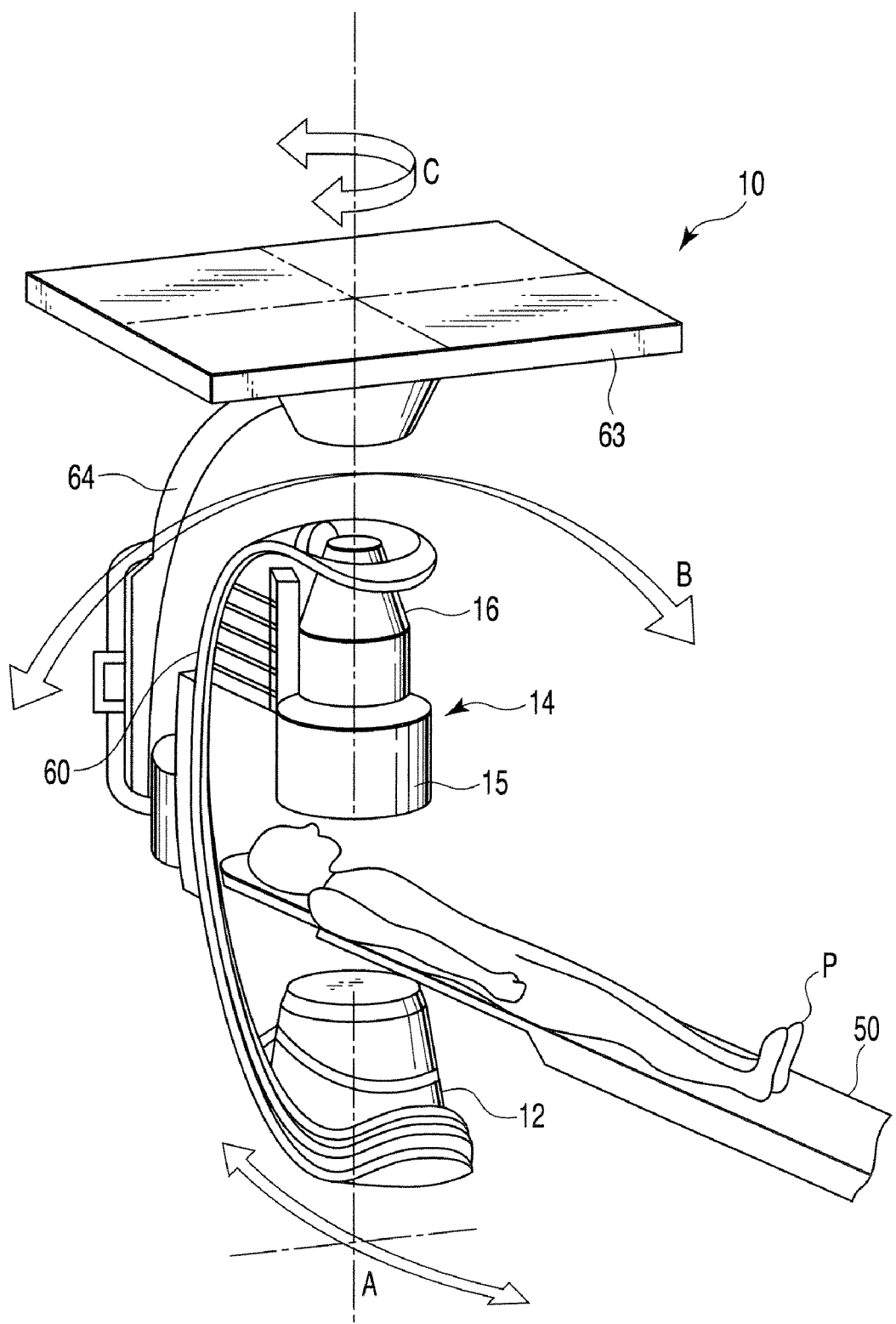
FIG. 2 is a perspective view of an X-ray imaging mechanism in FIG. 1.

As shown in FIG. 1, the X-ray angiography apparatus includes an X-ray imaging mechanism 10. As shown in FIG. 2, the X-ray imaging mechanism 10 includes an X-ray tube 12 and an X-ray detector 14. The X-ray detector 14 comprises an image intensifier 15 and a TV camera 16. The X-ray detector 14 comprises a flat panel detector (FPD: flat X-ray detector) having semiconductor detection elements arranged in the form of a matrix. The X-ray tube 12 and the X-ray detector 14 are mounted on a C-arm 60 in directions to face each other. A subject P on a top 50 of a bed is placed between the X-ray tube 12 and the X-ray detector 14. A column 64 suspended from a ceiling base 63 supports the C-arm 60. The C-arm 60 can rotate about three orthogonal axes A, B, and C. A rotation driving unit 22 is housed in the column 64. The rotation driving unit 22 includes two drive sources for independently rotating the C-arm 60 in the directions indicated by arrows A and B.

The X-ray angiography apparatus includes, in addition to the X-ray imaging mechanism 10, a system controller 20, a camera controller 21, a rotation controller 23, a first image memory 24, a second image memory 25, a sensitivity correction unit 26, a corresponding image selecting unit 19, a subtraction unit 27, a body thickness identifying unit 28, a scattered radiation correction unit 29, a beam hardening correction unit 30, a filtering unit 31 which performs high-frequency enhancement filtering, an affine transformation unit 32 which performs image enlargement/movement and the like, an image combining unit 33, a three-dimensional reconstruction unit 34, a three-dimensional image processing unit 35, a D/A conversion unit 36, and a display unit 37. The first image memory 24 is provided to store data concerning a plurality of mask images taken before contrast medium injection. The second image memory 25 is provided to store data concerning a plurality of contrast images taken after contrast medium injection. The corresponding image selecting unit 19 selects a mask image taken before contrast medium injection in a direction which coincides with or is nearest to the direction of each of a plurality of contrast images taken after contrast medium injection in subtraction imaging directions. The subtraction unit 27 generates a plurality of differential images at subtraction imaging angles by calculating differences (subtracting) between a plurality of contrast images and a plurality of mask images, selected by the corresponding image selecting unit 19, at the same or nearest angles. The three-dimensional reconstruction unit 34 reconstructs a three-dimensional blood vessel image on the basis of the plurality of differential images. The three-dimensional reconstruction unit 34 also reconstructs a three-dimensional image of a non-blood vessel portion having a bone and soft portion on the basis of the plurality of mask images. The body thickness identifying unit 28 identifies the thickness of a bone region and the thickness of a soft tissue region on an X-ray trajectory for each pixel of each mask image on the basis of the three-dimensional non-blood vessel image of the bone, soft tissue, and the like which is reconstructed by the three-dimensional reconstruction unit 34.

Figure 3:
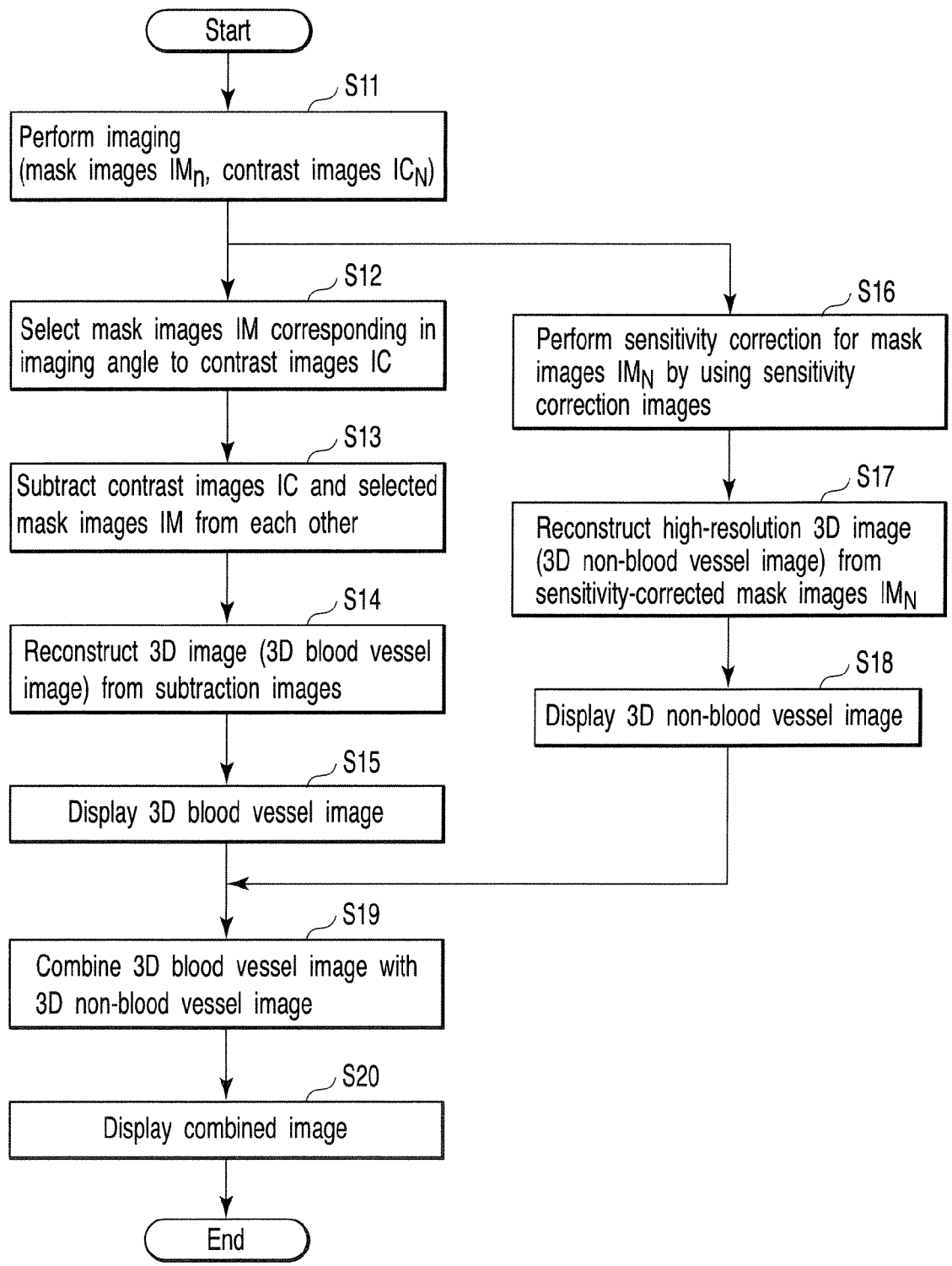
FIG. 3 is a flowchart showing a processing procedure in this embodiment.

The scattered radiation correction unit 29 performs scattered radiation correction for the original mask images on the basis of the thickness of the soft tissue or the thicknesses of the soft tissue and bone region. The beam hardening correction unit 30 performs beam hardening correction for the scatter-corrected mask images on the basis of the identified thickness of the soft tissue or the identified thicknesses of the soft tissue and bone region. The three-dimensional reconstruction unit 34 reconstructs a high-resolution three-dimensional non-blood vessel image on the basis of the plurality of mask images having undergone scattered radiation correction and beam hardening correction. The image combining unit 33 combines the three-dimensional blood vessel image generated by the three-dimensional reconstruction unit 34 with the three-dimensional non-blood vessel image. The combined three-dimensional image is configured to discriminate and manage the blood vessel image information and the non-blood vessel image information. The combined three-dimensional image is sent to the three-dimensional image processing unit 35 to generate a 2D combined image on axial planes for display by fusing axial non-blood vessel image with axial blood vessel image, or to generate a combined image of volume rendering blood vessel image and axial non-blood vessel image. The display unit 37 displays the combined image by itself or together with a slice image of the combined image through the D/A conversion unit 36. The operation of this embodiment will be described next with reference to FIG. 3. The C-arm 60 can rotate at high speed like a propeller by using the motor of the rotation driving unit 22. This makes it possible for the C-arm 60 to rotate around a subject through an angle of 180° or more in a short period of time.

In imaging step S11, mask image data are acquired before the injection of a contrast medium. The system controller 20 determines, on the basis of a control signal from an injector (not shown), whether a contrast medium has been injected.

Figure 4:
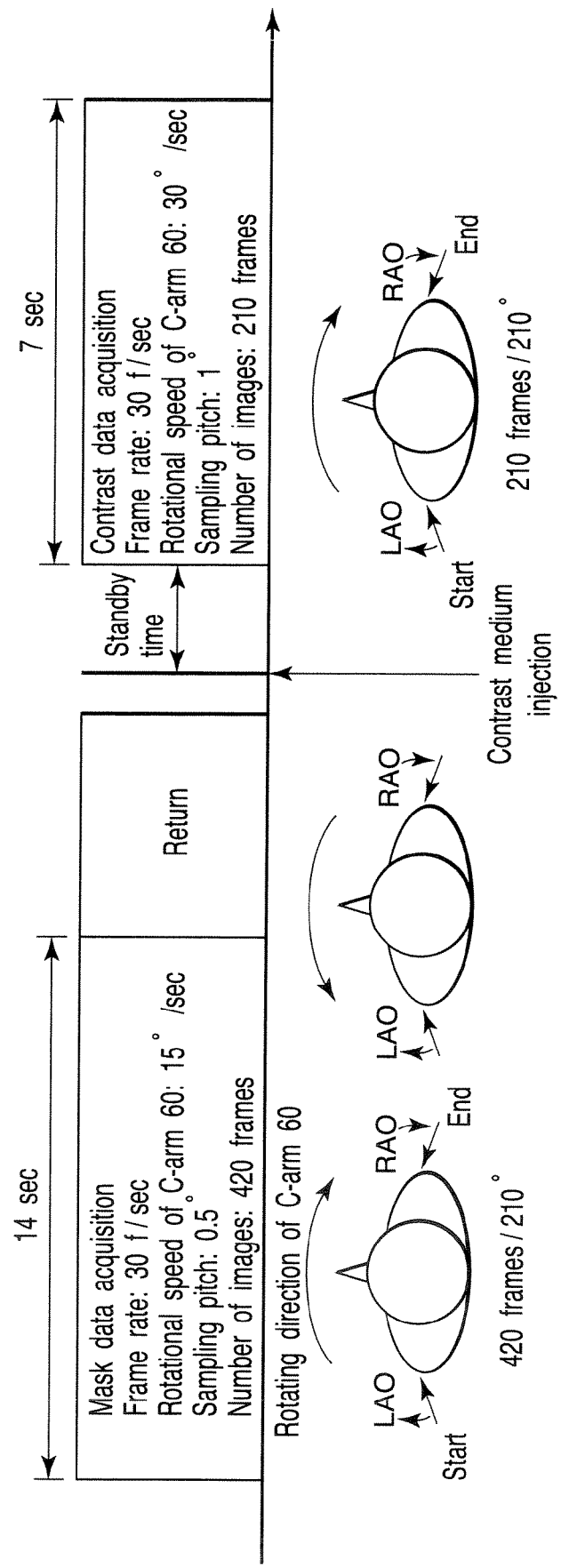
FIG. 4 is a view for supplementary explanation of a first imaging mode in imaging step S11 in FIG. 3.

As is illustrated in FIG. 4, the C-arm 60 rotates from the start position to the end position at a constant speed. The angle defined between the start position and the end position is, for example, 210°. While the C-arm 60 rotates, imaging is repeated at predetermined constant angle intervals. The camera controller 21 repeatedly reads out the data of mask images from the X-ray detector 14 in a predetermined period. Imaging conditions in this mask image imaging period are set such that the frame rate is 30 f/sec, the rotational speed of the C-arm 60 is 15° sec, the angle sampling pitch of mask images is 0.5°, and the number of frames imaged is 420. The first image memory 24 stores the data of 420 mask images (frames) IM in association with the data of the respective imaging angles. The C-arm 60 returns to a reference position at high speed after the imaging of mask images.

Note that this returning operation can be omitted. That is, the rotation of the C-arm 60 for the acquisition of contrast data may be in a direction reverse to that of the C-arm 60 for the acquisition of mask data.

When a proper standby time has elapsed since the injection of the contrast medium, an acquisition step for contrast image data starts. The C-arm 60 rotates from the start position to the end position at a constant speed through the same angle, i.e., 210°, as that in the mask image imaging period. While the C-arm 60 rotates, imaging is repeated at predetermined constant angle intervals. The camera controller 21 repeatedly reads the data of contrast images from the X-ray detector 14 in a predetermined cycle. Imaging conditions in this contrast image imaging period are set such that the frame rate is 30 f/sec, the rotational speed of the C-arm 60 is 30 f/sec, the angle sampling pitch(sampling angle pitch) of contrast images is 1°, and the number of frames imaged is 210. The second image memory 24 stores the data of 210 contrast images (frames) IC in association with the data of the respective imaging angles.

As compared with the imaging conditions for mask image data, the imaging conditions for contrast image data are set such that the frame rate is equal and the rotational speed of the C-arm 60 is twice. This makes the angle sampling pitch of contrast images become twice that of mask images. In addition, since the same imaging range (210°) is set, the time (seven sec) required to take a predetermined number of contrast images becomes half the time (14 sec) required to take a predetermined number of mask images. Furthermore, the number of contrast images (frames) taken is 210, which is half the number (420) of mask images taken.

Figure 5:
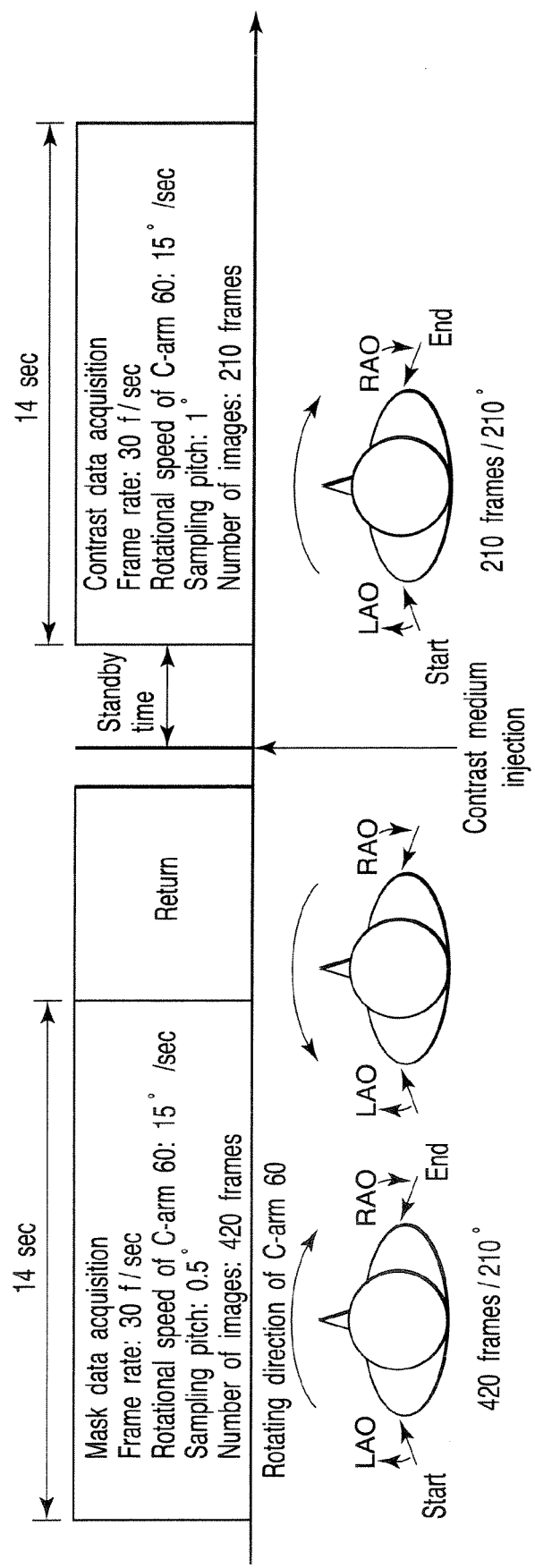
FIG. 5 is a view for supplementary explanation of a second imaging mode in imaging step S11 in FIG. 3.

Note that the operator can switch the imaging mode shown in FIG. 4 to the imaging mode shown in FIG. 5. In the imaging mode shown in FIG. 5, as compared with the imaging conditions in the mask image imaging step, the imaging conditions in the contrast image imaging step are set such that the rotational speed of the C-arm 60 is equal, and the frame rate of contrast images is ½ that of mask images. Consequently, as in the imaging mode shown in FIG. 4, the angle sampling pitch of contrast images is twice that of mask images, and the number of contrast images (frames) taken is 210, which is half the number (420) of mask images taken. The time (14 sec) required to take a predetermined number of contrast images becomes equal to the time (14 sec) required to take a predetermined number of mask images.

After the imaging operation, the corresponding image selecting unit 19 selects 210 mask images ($IM_n$), from the 420 mask images, each of which is equal in imaging angle to a corresponding one of the 210 contrast images ($IC_N$) (S12). The 210 contrast images ($IC_N$) and the selected 210 mask images ($IM_n$) are subtracted from each other at the same imaging angles (S13). The three-dimensional reconstruction unit 34 reconstructs a three-dimensional image on the basis of the 210 differential images generated in step S13 (S14). This three-dimensional image is called a three-dimensional blood vessel image because it mainly represents a blood vessel form as a contrasted region, from which a mainly non-blood vessel region such as a non-contrasted bone or soft tissue is removed, thereby discriminating it from a three-dimensional non-blood vessel image which mainly represents a bone or soft tissue form to be described later.

The filtered back projection method proposed by Feldkamp et al. will be exemplified as a reconstruction method. A proper convolution filter such as a Shepp & Logan or Ramachandran filter is applied to 210 DSA images. Performing back projection computation will obtain reconstruction data. In this case, a reconstruction region is defined as a cylinder inscribing an X-ray beam in all the directions of the X-ray tube 12. It is necessary to three-dimensionally discretize the inside of this cylinder with, for example, a length $\underline{d}$ of the central portion of a reconstruction region projected on the width of one detection element of the X-ray detector 14 and to obtain a reconstructed image formed by data at discrete points. This is an example of discretization intervals, which vary depending on apparatuses. Therefore, it basically suffices to use discretization intervals defined by the apparatus to be used.

The reconstructed image is transferred to a three-dimensional image display unit and three-dimensionally displayed by a method such as volume rendering (S15).

High-resolution three-dimensional non-blood vessel image generation and display processing in steps S16 to S18 is performed in parallel with or before or after this three-dimensional blood vessel image generation and display processing in steps S12 to S15. A three-dimensional non-blood vessel image is generated by using all the acquired 420 mask images ($IM_n$). First of all, the sensitivity correction unit 26 performs sensitivity correction for the 420 mask images ($IM_n$) (S16). Sensitivity correction processing is performed by subtracting, from the respective mask images ($IM_n$) from projection images which are acquired in advance by imaging a homogeneous phantom, represent a spatial distribution of sensitivity within a detection surface associated with the X-ray detector 14, and are held in a storage unit in the sensitivity correction unit 26. Note that the 420 sensitivity-corrected mask images are represented by P(θ, i, j), where θ represents a rotational angle at the time of imaging, and (i, j) represents a two-dimensional position. A three-dimensional non-blood vessel image is reconstructed on the basis of the 420 sensitivity-corrected mask images P(θ, i, j) (S17). The reconstruction of this high-resolution three-dimensional non-blood vessel image uses beam hardening correction and scattered radiation correction.

Figure 6:
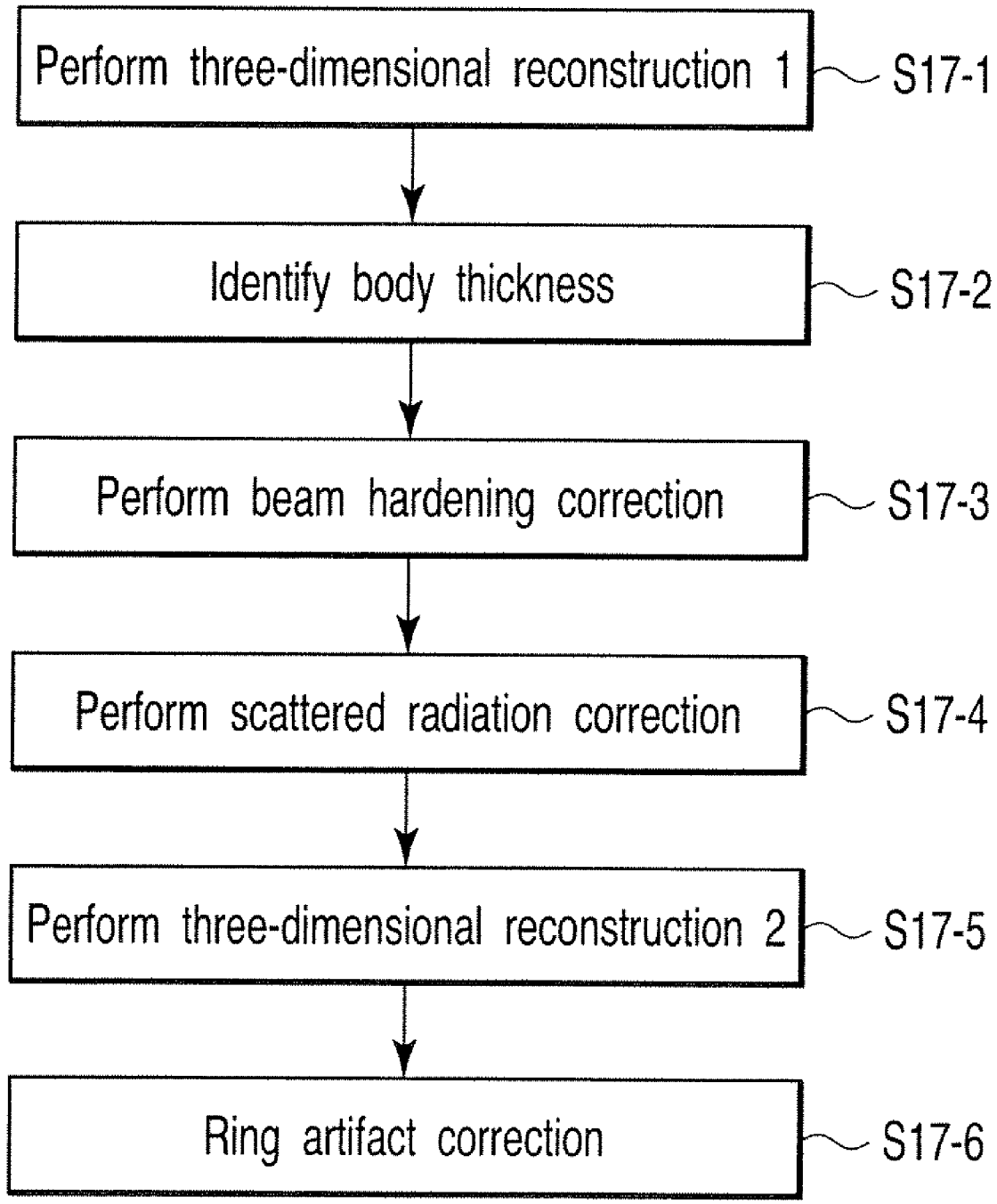
FIG. 6 is a flowchart showing a detailed processing procedure in three-dimensional non-blood vessel image reconstruction step S17 in FIG. 3.

FIG. 6 shows a detailed processing procedure for the high-resolution three-dimensional non-blood vessel image reconstruction processing in step S17. First of all, the three-dimensional reconstruction unit 34 reconstructs a preliminary three-dimensional non-blood vessel image from all 420 sensitivity-corrected images or, for example, about 210 or 100 mask images P(θ, i, j) extracted therefrom at predetermined intervals of rotational angles (S17-1). This preliminary three-dimensional non-blood vessel image is an image which does not aim for the observation of the image itself for the purpose of interpretation but aims for body thickness identification to be described later. Therefore, it suffices to reconstruct such an image by using some of all the 420 images or reduce the reconstruction matrix for the reconstruction processing in step S17-6 to be described later.

The body thickness identifying unit 28 then performs threshold processing for the preliminary three-dimensional non-blood vessel image to separate a bone portion, a soft tissue portion, and a background region, and calculates a thickness B(θ, i, j) of the bone portion and a thickness T(θ, i, j) of the soft tissue on an X-ray trajectory for each mask image and for each pixel of each mask image (S17-2).

Figure 7:
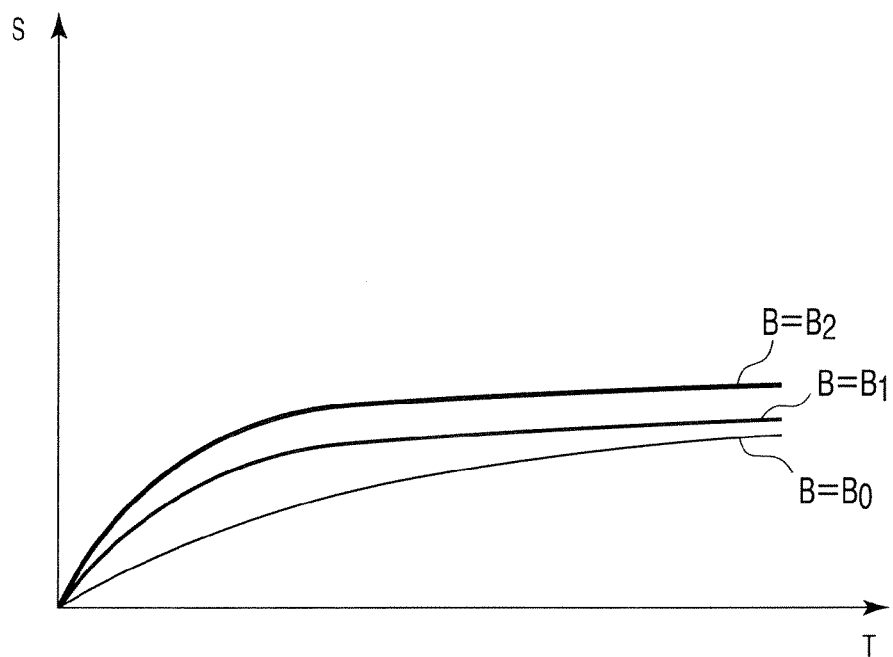
FIG. 7 is a graph showing an example of correction values held by a beam hardening correction unit in FIG. 1.

Subsequently, the scattered radiation correction unit 29 receives the mask image P(θ, i, j) together with the calculated thickness data B(θ, i, j) and T(θ, i, j) and performs scattered radiation correction for them (S17-3). The scattered radiation correction unit 29 performs scattered radiation correction for a pixel value for each mask image and for each pixel of each mask image by referring to the two-dimensional correction table by using the thicknesses of the bone and soft tissue.

$$P_c(\theta,i,j)=P(\theta,i,j)-S(B,T)$$

where $P_c$(θ, i, j) represents a mask image subjected to scattered radiation correction, and S(B, T) represents a scattered radiation correction coefficient (1−γ) determined by a scattered radiation content γ. The thickness B of the bone portion and the thickness T of the soft tissue determine this coefficient (assuming that the thicknesses of the bone in a peripheral portion and soft tissue are almost constant). This correction table is experimentally obtained and held in the storage unit of the scattered radiation correction unit 29. FIG. 7 exemplifies correspondence between the thickness T of the soft tissue and the correction value S for each thickness B of the bone portion (FIG. 7 exemplifies three kinds of thicknesses, i.e., B0 (bone thickness of 0), B1 (bone thickness of 1 cm), and B2 (bone thickness of 2 cm)). The discrete values of this graph are held in the form of a correction table. The correction table is configured to receive the thickness B of the bone portion and the thickness T of the soft tissue and output the scattered radiation correction coefficient S. In practice, the scattered radiation correction coefficient S is calculated by interpolation from a plurality of correction coefficient candidates approximating to the calculated thicknesses B and T of the bone portion and soft tissue.

Figure 8:
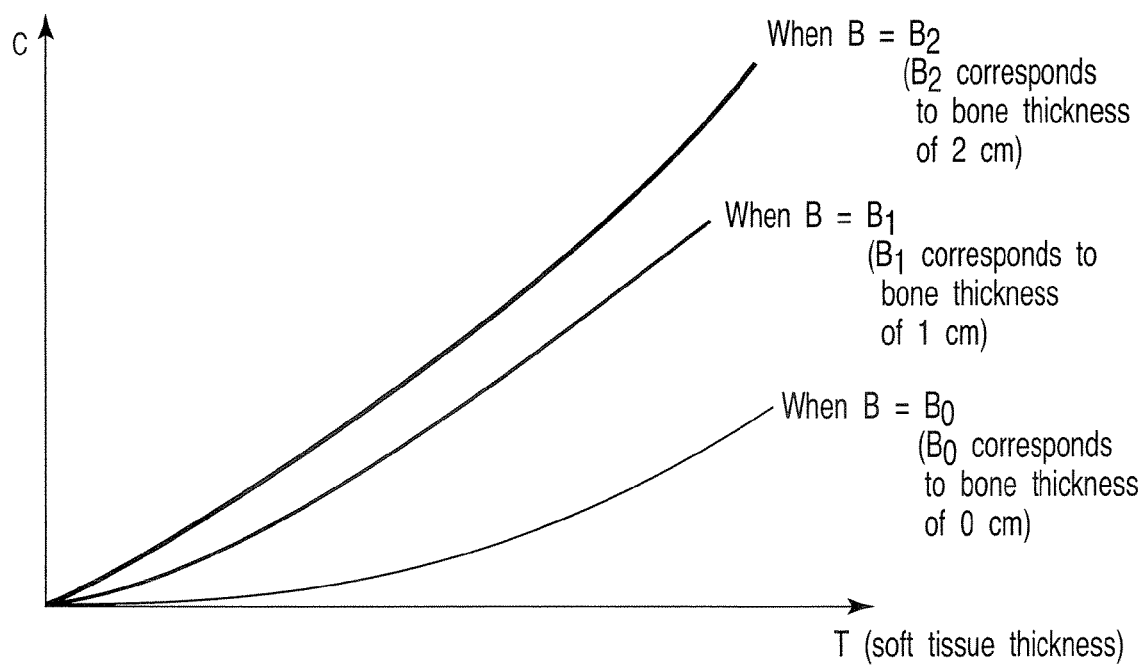
FIG. 8 is a graph showing an example of correction values held by a scattered radiation correction unit in FIG. 1.

The thickness data B(θ, i, j) and T(θ, i, j) and scatter corrected mask image $P_c$(θ, i, j) are then sent to the beam hardening correction unit 30. First of all, the beam hardening correction unit 30 corrects a pixel value for each mask image and for each pixel of each mask image as follows by referring to a two-dimensional correction table on the basis of the calculation results (S17-4).

$$P_a(\theta,i,j)=P_c(\theta,i,j)+C(B,T)$$

where $P_a(\theta, i, j)$ is a beam hardening and scatter corrected mask image, and $C(B, T)$ is a correction value corresponding to the thickness of the bone portion and the thickness of the soft tissue. $B(\theta, i, j)$ and $T(\theta, i, j)$ respectively represent the thicknesses of the bone and soft tissue, and a correction value is determined for each of these thicknesses. This correction table is also experimentally obtained in advance and held in the storage unit of the beam hardening correction unit 30. FIG. 8 exemplifies the correspondence between the thickness T of the soft tissue and the correction value C for each thickness B of the bone portion (FIG. 8 exemplifies three kinds of thicknesses, i.e., B0 (bone thickness of 0), B1 (bone thickness of 1 cm), and B2 (bone thickness of 2 cm)). The discrete values of this graph are held in the form of a correction table. The correction table is configured to receive the thickness B of the bone portion and the thickness T of the soft tissue and output the correction value C. In practice, a correction value is calculated by interpolation from a plurality of correction value candidates approximating to the calculated thicknesses B and T of the bone portion and soft tissue. Note that this embodiment has exemplified the beam hardening correction method and scattered radiation correction method using reconstructed images. However, the present invention is not limited to this, and may use a method of correcting one or both of the above values from only projection data. Such a method has the merit of shortening the calculation time because there is no need to reconstruct a non-blood vessel image once. Although this method generally performs correction assuming that an absorbing material which contributes to projection data is a soft tissue, the method has a demerit that it cannot properly perform correction for a portion, e.g., a head, to which a bone greatly contributes.

The three-dimensional reconstruction unit 34 reconstructs a high-resolution three-dimensional non-blood vessel image on the basis of the 420 mask images $P_a(\theta, i, j)$ having undergone beam hardening correction and scattered radiation correction (S17-5).

The high-resolution three-dimensional non-blood vessel image is sent to the ring artifact correcting unit 38, and then ring-artifacts are removed with well-known technique as one of CT's correction methods (S17-6).

The ring-artifacts free high-resolution three-dimensional non-blood vessel image is transferred to the image combining unit 33. Note that the transferred image has additional information explicitly expressing that the image is a target image for image combining operation. If, therefore, the transferred information has this additional information, the image combining unit 33 combines the three-dimensional non-blood vessel image reconstructed in step S17 with the three-dimensional blood vessel image reconstructed in step S14 (S19). The three-dimensional image processing unit 35 forms the combined image into a two-dimensional image by a method like volume rendering (S20). At the same time, the display unit 37 displays a slice image (e.g., an axial, coronal, or saggital image) of the combined three-dimensional image (S20). In combining and displaying the three-dimensional non-blood vessel image and the three-dimensional blood vessel image, the display unit 37 displays them while changing colors displaying different volumes and making the positional relationship between the non-blood vessel system and the blood vessels be easily comprehended. At the same time, the display unit 37 separately displays them as the operator presses a switch. The switch allows to switch between three modes, namely a combined display mode, blood vessel display mode, and non-blood vessel display mode. Such switches independently exist as a switch for three-dimensional image processing and a switch for cross-sectional images. Sliders for controlling the assignment of weights to a blood vessel image and a non-blood vessel image at the time of combined display operation independently exist as a switch for three-dimensional image processing and a switch for cross-sectional images. When the slider is located at the center position, the display unit 37 displays both a blood vessel image and a non-blood vessel image. As the slider moves to the left, the weight assigned to the non-blood vessel portion changes from 1 to 0, and the display of the non-blood vessel portion gradually fades. In contrast, as the slider moves to the right, the weight assigned to the blood vessel portion changes from 1 to 0, and the display of the blood vessel portion gradually fades. Note that it is possible to independently change the display conditions (color, optical parameters, window level/window width, and the like) of each volume. In addition, it is possible to perform processing such as cutting for each volume separately.

This apparatus acquires contrast images at a coarse angle sampling pitch in a contrast image acquisition period, and acquires mask images at a fine angle sampling pitch in a mask image acquisition period. The apparatus separately performs two types of reconstruction processing using these two types of images. One type of reconstruction processing is for non-blood vessel images using only mask images. The other type of reconstruction processing is for blood vessel images based on DSA using mask and contrast images. This makes it possible to observe a blood vessel structure and acquire a high-resolution non-blood vessel image, thus improving the visibility of a soft tissue. The conventional method of improving the visibility of a soft tissue is a method of simultaneously visualizing blood vessel information, a soft tissue, and a bone tissue, and hence receives the great influences of changes in the flow rate of a contrast medium due to the pumping function of the heart and artifacts originating from the injection timing of a contrast medium. In contrast, the present invention separately reconstruct blood vessel information and non-blood vessel information, and hence the non-blood vessel information is free from the influence of artifacts originating from blood vessels. This improves the image quality of both a blood vessel portion and a non-blood vessel portion as compared with the conventional method. In addition, in the current situation where the image reading rate of the detector is considerably limited, the conventional method requires a long period of time for imaging to finely visualize non-blood vessel information. In practice, making a contrast medium flow for such a long period of time imposes a heavy burden on the patient, and results in huge artifacts due to contrast medium. It is therefore necessary to acquire blood vessel information in a short period of time in general. This makes it impossible to acquire such a long period of time in practical, and to visualize non-blood vessel information with high accuracy. In contrast, at the time of imaging, the present invention acquires images slowly in a long period of time when performing non-blood vessel information imaging and also acquires images quickly in a short period of time when performing blood vessel information imaging. This makes it possible to acquire high-resolution non-blood vessel images while observing a blood vessel structure. Finally, combining these images makes it possible to merge the two types of information.

Figure 9:
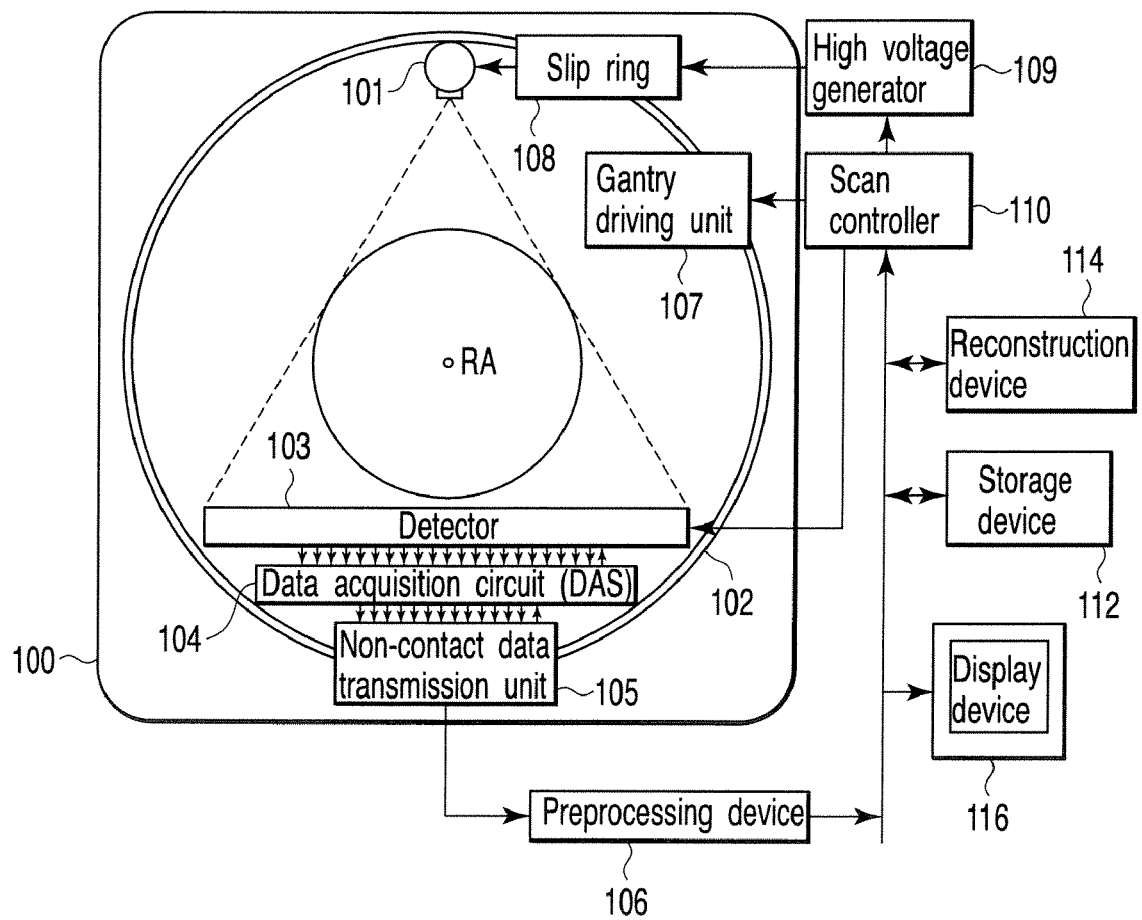
FIG. 9 is a view showing the arrangement of an X-ray computed tomographic apparatus according to a modification of this embodiment.

Note that a modification of this embodiment includes an application to an X-ray computed tomographic apparatus. As shown in FIG. 9, a gantry 100 includes an X-ray tube 101 and an X-ray detector 103. The X-ray tube 101 and the X-ray detector 103 are mounted on an annular frame 102 supported to be rotatable about a rotation axis RA. The X-ray detector 103 faces the X-ray tube 101. A gantry driving unit 107 continuously rotates the frame 102 at a high speed of, for example, 0.4 sec/revolution. A high voltage generator 109 applies a tube voltage to the X-ray tube 101 through a slip ring 108 and supplies a filament current to the X-ray tube 101. With this operation, the X-ray tube 101 generates X-rays. The X-ray detector 103 detects X-rays transmitted through the subject.

A data acquisition circuit 104 generally called a DAS (Data Acquisition System) converts a signal output from the X-ray detector 103 for each channel, amplifies it, and converts it into a digital signal. This data (raw data) is sent to preprocessing device 106 housed in the external console of the gantry 100 through a non-contact data transmission unit 105, and undergoes correction processing such as sensitivity correction. A storage device 112 then stores the resultant data as so-called projection data immediately before reconstruction processing. The storage device 112 connects to a scan controller 110 through a data/control bus, together with a reconstruction device 114 which reconstructs a tomographic image from projection data and a display device 116 which display the tomographic image.

The scan controller 110 changes some of scan conditions between a mask projection data acquisition period before contrast medium injection and a contrast projection data acquisition period after contrast medium injection. The rotational speeds of the X-ray tube 101 and X-ray detector 103 in a contrast projection data acquisition period are set to the same as those in a mask projection data acquisition period. The data reading cycle of the X-ray detector 103 in a contrast projection data acquisition period is, for example, double that in a mask projection data acquisition period. As a result, the angle sampling pitch (also called the view pitch) at which projection data are acquired in a contrast projection data acquisition period is increased by twice that in a mask projection data acquisition period. In other words, the number of sampling points (also called view points) at which projection data are acquired in a contrast projection data acquisition period is decreased to ½ that in a mask projection data acquisition period. Typically, X-rays are continuously generated in a contrast projection data acquisition period and a mask projection data acquisition period. It suffices, however, to generate pulse X-rays in a contrast projection data acquisition period and generate continuous X-rays in a mask projection data acquisition period.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray angiography apparatus comprising:
   a C-arm;
   a support mechanism which rotatably supports the C-arm;
   a rotation driving unit which drives rotation of the C-arm;
   an X-ray tube which is mounted on one end of the C-arm;
   an X-ray detector which is mounted on the other end of the C-arm in a direction to face the X-ray tube; and
   a control unit which controls the X-ray detector to make a frame rate of the X-ray detector be the same in a mask image imaging period in which a plurality of mask images are taken and in a contrast image imaging period in which a plurality of contrast images are taken, and controls the rotation driving unit to make a rotational speed of the C-arm in the contrast image imaging period become higher than the rotational speed of the C-arm in the mask image imaging period.

2. An apparatus according to claim 1, further comprising a reconstruction unit which reconstructs a first three-dimensional image on the basis of differential images between the contrast images and the mask images, and reconstructs a second three-dimensional image on the basis of the mask images.

3. An apparatus according to claim 1, further comprising an image generating unit which reconstructs a first three-dimensional image on the basis of said plurality of contrast images, reconstructs a second three-dimensional image on the basis of some of said plurality of mask images, reconstructs a third three-dimensional image on the basis of a remainder of said plurality of mask images, generates a fourth three-dimensional image by subtracting the second three-dimensional image from the first three-dimensional image, and generates a fifth three-dimensional image by adding the second three-dimensional image to the third three-dimensional image.

4. An apparatus according to claim 1, further comprising an image generating unit which reconstructs a first three-dimensional image on the basis of said plurality of contrast images, reconstructs a second three-dimensional image on the basis of some of said plurality of mask images, reconstructs a third three-dimensional image on the basis of said plurality of mask images, and generates a fourth three-dimensional image by subtracting the second three-dimensional image from the first three-dimensional image.

5. An apparatus according to claim 2, further comprising an image generating unit which generates a combined image of the first three-dimensional image and the second three-dimensional image, and generates a combined image of a slice originating from the first three-dimensional image and a slice originating from the second three-dimensional image.

6. An apparatus according to claim 5, further comprising a display unit which displays the first three-dimensional image, the second three-dimensional image, and the combined image while switching the images in accordance with an operator instruction.

7. An apparatus according to claim 5, wherein the image generating unit includes a function of changing a combining ratio between the first three-dimensional image and the second three-dimensional image.

8. An apparatus according to claim 6, wherein the image generating unit displays the first three-dimensional image and the second three-dimensional image in the combined image in different color systems.

9. An apparatus according to claim 2, wherein the reconstruction unit includes correction means for performing at least one of beam hardening correction, scattered radiation correction, and ring artifact correction on the basis of the mask images, and means for reconstructing a third three-dimensional image on the basis of the mask images subjected to the correction.

10. An apparatus according to claim 9, wherein the correction means includes means for reconstructing a fourth three-dimensional image by using data of some of the mask images, means for identifying a thickness of a bone region and a thickness of a soft tissue region from the fourth three-dimensional image by threshold processing, means for performing at least one of beam hardening correction and scattered radiation correction for the mask images on the basis of the identified thickness of the bone region and the identified thickness of the soft tissue region, and means for reconstructing a fifth three-dimensional image on the basis of the mask images subjected to the correction.

11. An apparatus according to claim 10, wherein the fourth three-dimensional image is lower in resolution than the second three-dimensional image.

12. An apparatus according to claim 10, wherein the means for reconstructing a fourth three-dimensional image by using data of some of the mask images comprises means for performing reconstruction by using either or both of some frames of mask images and images obtained by reducing the mask images.

13. An apparatus according to claim 1, wherein an angle sampling pitch of the contrast images is not less than twice an angle sampling pitch of the mask images.

14. An X-ray angiography apparatus comprising:
a C-arm;
a support mechanism which rotatably supports the C-arm;
a rotation driving unit which drives rotation of the C-arm;
an X-ray tube which is mounted on one end of the C-arm;
an X-ray detector which is mounted on the other end of the C-arm in a direction to face the X-ray tube; and
a control unit which controls the X-ray detector and the rotation driving unit to make an angle sampling pitch of a plurality of contrast images become larger than an angle sampling pitch of a plurality of mask images.

15. An X-ray angiography apparatus comprising:
a C-arm;
a support mechanism which rotatably supports the C-arm;
a rotation driving unit which rotates the C-arm;
an X-ray tube which is mounted on one end of the C-arm;
an X-ray detector which is mounted on the other end of the C-arm in a direction to face the X-ray tube; and
a control unit which controls the X-ray detector such that a frame rate of the X-ray detector in a contrast image imaging period in which a plurality of contrast images are taken becomes higher than the frame rate of the X-ray detector in a mask image imaging period in which a plurality of mask images are taken.

16. An X-ray angiography apparatus comprising:
a C-arm;
a support mechanism which rotatably supports the C-arm;
a rotation driving unit which drives rotation of the C-arm;
an X-ray tube mounted on the C-arm;
an X-ray detector mounted on the C-arm in a direction to face the X-ray tube; and
a control unit which controls the rotation driving unit to make a rotational speed of the C-arm in a contrast image imaging period become higher than the rotational speed of the C-arm in a mask image imaging period.

17. An X-ray angiography apparatus comprising:
a C-arm;
a support mechanism which rotatably supports the C-arm;
a rotation driving unit which drives rotation of the C-arm;
an X-ray tube which is mounted on one end of the C-arm;
an X-ray detector which is mounted on the other end of the C-arm in a direction to face the X-ray tube; and
a control unit which controls the X-ray detector and the rotation driving unit such that an angle sampling pitch at which a plurality of first images are acquired becomes larger than an angle sampling pitch at which a plurality of second images are acquired.

18. An X-ray angiography apparatus comprising:
a C-arm;
a support mechanism which rotatably supports the C-arm;
a rotation driving unit which drives rotation of the C-arm;
an X-ray tube which is mounted on one end of the C-arm;
an X-ray detector which is mounted on the other end of the C-arm in a direction to face the X-ray tube; and
a control unit which controls the rotation driving unit to make a rotational speed of the C-arm in a contrast image imaging period the same with the rotational speed of the C-arm in a mask image imaging period, and controls the X-ray detector to make a frame rate of the X-ray detector in a contrast image imaging period in which a plurality of contrast images are taken lower than that in a mask image imaging period in which a plurality of mask images are taken.

19. An apparatus according to claim 18, wherein an X-ray in a contrast image imaging period in which a plurality of contrast images are taken is irradiated discretely, and an X-ray in a mask image imaging period in which a plurality of mask images are taken is irradiated continuously.

20. An X-ray computed tomographic apparatus comprising:
an X-ray tube which generates X-rays;
an X-ray detector which detects X-rays transmitted through a subject;
a rotating mechanism which rotates the X-ray tube and the X-ray detector;
a reconstruction processing unit which reconstructs an image on the basis of an output from the X-ray detector; and
a control unit which controls the X-ray detector so as to change an angle sampling pitch at which projection data are acquired before and after contrast medium injection.

* * * * *